(12) United States Patent
Sickinger et al.

(10) Patent No.: US 6,926,866 B2
(45) Date of Patent: Aug. 9, 2005

(54) METHOD AND DEVICE FOR SEPARATING SAMPLES FROM A LIQUID

(75) Inventors: Anselm Sickinger, Leipzig (DE);
Hanspeter Romer, Wolfhausen (CH);
Nikolaus Ingenhoven, Uerikon (CH);
Urs Knecht, Hombrechtikon (CH)

(73) Assignee: Tecan Trading AG, Männedorf (CH)

( * ) Notice: Subject to any disclaimer, the term of this patent is extended or adjusted under 35 U.S.C. 154(b) by 447 days.

(21) Appl. No.: 09/992,304

(22) Filed: Nov. 19, 2001

(65) Prior Publication Data

US 2002/0095240 A1 Jul. 18, 2002

(30) Foreign Application Priority Data

Nov. 17, 2000 (CH) .............................................. 2252/00

(51) Int. Cl.⁷ .......................... B01L 3/02; G01N 21/00; G05D 9/00; G05D 11/00; G05D 23/00
(52) U.S. Cl. .......................... 422/100; 422/106; 422/67; 700/266; 700/281; 700/282; 700/283
(58) Field of Search ................................ 422/100, 106, 422/67; 700/266, 281–283

(56) References Cited

U.S. PATENT DOCUMENTS

| | | | |
|---|---|---|---|
| 5,763,278 A | 6/1998 | Sickinger et al. | |
| 5,916,524 A | 6/1999 | Tisone | |
| 5,927,547 A | 7/1999 | Papen et al. | |
| 6,060,320 A * | 5/2000 | Dorenkott et al. | 436/54 |
| 6,063,339 A | 5/2000 | Tisone et al. | |
| 6,203,759 B1 * | 3/2001 | Pelc et al. | 422/100 |
| 6,256,643 B1 * | 7/2001 | Cork et al. | 707/205 |
| 6,261,521 B1 * | 7/2001 | Mimura et al. | 422/67 |
| 6,349,264 B1 * | 2/2002 | Rhett et al. | 702/19 |
| 6,589,791 B1 * | 7/2003 | LaBudde et al. | 436/55 |
| 6,620,625 B2 * | 9/2003 | Wolk et al. | 436/180 |
| 6,647,397 B2 * | 11/2003 | Parce | 707/104.1 |
| 6,735,531 B2 * | 5/2004 | Rhett et al. | 702/31 |
| 2001/0048899 A1 * | 12/2001 | Marouiss et al. | 422/100 |
| 2002/0064482 A1 * | 5/2002 | Tisone et al. | 422/100 |
| 2003/0012081 A1 * | 1/2003 | Jungmann et al. | 366/141 |
| 2003/0049863 A1 * | 3/2003 | Woodward | 436/180 |
| 2003/0149505 A1 * | 8/2003 | Mogensen | 700/117 |
| 2003/0163088 A1 * | 8/2003 | Blomquist | 604/131 |
| 2003/0163223 A1 * | 8/2003 | Blomquist | 700/282 |
| 2003/0215957 A1 * | 11/2003 | Lemmo et al. | 436/180 |
| 2003/0229422 A1 * | 12/2003 | Martens et al. | 700/266 |
| 2003/0236592 A1 * | 12/2003 | Shajii et al. | 700/282 |
| 2004/0014227 A1 * | 1/2004 | Frederick et al. | 436/43 |
| 2004/0015269 A1 * | 1/2004 | Jungmann et al. | 700/283 |
| 2004/0018635 A1 * | 1/2004 | Peck et al. | 436/180 |
| 2004/0039488 A1 * | 2/2004 | Junk et al. | 700/282 |
| 2004/0076546 A1 * | 4/2004 | Bissett | 422/68.1 |
| 2004/0077996 A1 * | 4/2004 | Jasperson et al. | 604/67 |
| 2004/0087894 A1 * | 5/2004 | Flaherty | 604/65 |

FOREIGN PATENT DOCUMENTS

| | | |
|---|---|---|
| DE | 199 19 135 A | 11/2000 |
| EP | 0 725 267 A | 8/1996 |
| WO | WO 99 42804 A | 8/1999 |

* cited by examiner

*Primary Examiner*—Jill Warden
*Assistant Examiner*—Brian R. Gordon
(74) *Attorney, Agent, or Firm*—McDonnell Boehnen Hulbert & Berghoff LLP

(57) ABSTRACT

System, method, and computer program product for synchronizing a system for aspirating and/or dispensing of liquid samples that includes a microejection device and a pump, which are connected with one another via tubing, wherein a computer is capable of being loaded with an activatable computer program product for synchronizing operation of the microejection device and the pump. Embodiments are characterized in that the loaded and activated computer program product, directs the computer to control and synchronize the system: (a) to actively define a sample volume and dispense the defined sample volume using the microejection device, which is filled with sample liquid; and (b) to track a part of the pump that conveys liquid around a value, dependent on the sample volume, which is defined and is actively dispensed only by the microejection device, to prevent excessive pressure differences in the microejection device, tubing, and pump.

19 Claims, 1 Drawing Sheet

METHOD AND DEVICE FOR SEPARATING SAMPLES FROM A LIQUID

This application claims priority under 35 U.S.C. §119 to Swiss patent application no. 2000 2252/00, filed Nov. 17, 2000.

FIELD OF THE INVENTION

The present invention relates to a computer for synchronizing a system for aspirating and/or dispensing liquid samples that comprises a microejection device and a pump which are connected with one another via tubing, with this computer being implemented for loading an activatable computer program product for synchronizing the microejection device and pump. The present invention also concerns a corresponding system, method, and computer program product.

BACKGROUND OF THE INVENTION

It is known that droplets with a volume of more than 10 μl can be dispensed from the air very easily, since if the pipette is correctly manipulated, the droplets leave the pipette tip of their own accord. The droplet size is then determined by the physical properties of the sample liquid, such as surface tension or viscosity. The droplet size thus limits the resolution of the quantity of liquid to be dispensed.

The aspirating and dispensing, i.e. the pipetting of liquid samples with a volume of less than 10 μl, in contrast, typically requires instruments and techniques which guarantee the dispensing of such small samples. The dispensing of a liquid with a pipette tip, i.e. with the endpiece of a device for aspirating and/or dispensing sample liquid, can occur from the air ("from air") or by touching a surface. This surface can be the solid surface of a container ("on tip touch"), into which the liquid sample is to be dispensed. It can also be the surface of a liquid in this container ("on liquid surface"). A mixing procedure following the dispensing is recommended—particularly for very small sample volumes in the nanoliter or even picoliter range—so that uniform distribution of the sample volume in a diluent is ensured.

Disposable tips significantly reduce the danger of unintentional transfer of parts of the sample (contamination). Simple disposable tips are known (so-called "air-displacement tips"), whose geometry and material is optimized for the exact aspirating and/or dispensing of very small volumes. The use of so-called "positive-displacement tips", which have a pump plunger inside, is also known.

Systems for separating samples from a liquid are known as pipettors. Such systems serve, for example, for dispensing liquids into the wells of Standard Microtitration Plates™ (trademark of Beckman Coulter, Inc., 4300 N. Harbour Blvd., P.O. Box 3100 Fullerton, Calif., USA 92834) and/or microplates with 96 wells. The reduction of the sample volumes (e.g. for filling high-density microplates with 384, 864, 1536, or even more wells) plays an increasingly important role, with the precision of the sample volume dispensed being assigned a great importance. The elevation of the number of samples typically also requires miniaturization of the experiment, so that the use of a pipettor is necessary and special requirements must be placed on the precision of sample volumes and the accuracy of the movement control and/or of the dispensing of this pipettor.

The precision of a pipetting system is judged on the basis of the accuracy (ACC=accuracy) and reproducibility (CV=coefficient of variation) of the liquid samples dispensed. The reproducibility has greater significance assigned to it in this case, since systematic errors can, if necessary, be compensated by means of suitable correction parameters. In principle, two basic modes are differentiated in pipetting: single pipetting and multipipetting. In the single pipetting mode, a liquid sample is aspirated and dispensed at another location. In the multipipetting mode, a larger volume of liquid is aspirated at one time and subsequently dispensed in several—typically equivalent—portions (aliquots) at one or more different locations, e.g. in various wells of a Standard Microtitration Plate™.

Simpler pipettors, so-called "open systems", connect the reservoir for the liquid to be pipetted with the pipette tip via a line into which a dispensing pump can be inserted. The dispensing pumps are typically implemented as piston pumps. For aspirating the sample, only the pump is set into operation, the pipette tip merely passively relays the liquid flow. For dispensing a sample volume, the pump is then switched off or bridged. For example, a pipette tip in the form of a microejection pump is known from European Patent No. 0 725 267, with which a liquid sample is actively separated. The supply of the liquid occurs due to the hydrostatic pressure obtaining in the line between the reservoir and the pipette tip. Such systems are relatively economical, but they have the disadvantage that the hydrostatic pressure can vary within a wide range. The reproducible dispensing of very small volumes in the nanoliter or even picoliter range is impaired thereby.

In addition, a "closed" system of this class is known from U.S. Pat. No. 5,927,547. In this system as well, only the pump is set in operation for aspirating; the pipette tip merely passively relays the liquid flow. In this system, however, the dispensing pump is put in operation—for generating a specific pressure in the tubing system to the pipette tip—for dispensing the liquid. For separating volumes in the picoliter to nanoliter range, piezoelectric driven tips and/or microejection pumps—as also known from European Patent No. 0 725 267—are used, in which the liquid or sample volumes are actively ejected out of the pipette tip. The pressure between the dispensing pump and the pipette tip is monitored with a sensor. The feed of the dispensing pump of this rather expensive and complex system is then regulated via a pressure sensor and an attached processing unit. Thus, synchronization between the microejection pump and the dispensing pump occurs.

The determination of the sample volume with a valve located in the immediate vicinity of the pipette tip or in the pipette tip itself, which, for example, is implemented as a solenoid or a piezovalve and is opened briefly, is also known. In this case, an initial pressure is used in the system. This opening is known in single action form or also in intervals. For dispensing a defined volume, the initial pressure must be adjusted very exactly to the liquid properties and the atmospheric conditions (above all to the air pressure). The effects influence each other strongly, so that the system must be readjusted upon a change of the liquid and/or its properties or the surrounding conditions.

SUMMARY OF THE INVENTION

An object of the present invention is to provide devices and methods that allow both economical and highly reproducible separation of volumes in the nanoliter to picoliter range.

This object is achieved according to a first aspect with a system, according to a second aspect with a method, and according to a third aspect with a computer program product for synchronizing a system for aspirating and/or dispensing of liquid samples that comprises a microejection device and a pump, which are connected with one another via tubing, wherein this computer is capable of being loaded with an activatable computer program product for synchronizing operation of the microejection device and the pump. The invention is characterized in that the loaded and activated computer program product directs the computer to control and synchronize the system: (a) to actively define a sample volume and dispense the defined sample volume using the microejection device, which is filled with sample liquid; and (b) to track a part of the pump that conveys liquid around a value, dependent on the sample volume, which is defined and is actively dispensed only by the microejection device, to prevent excessive pressure differences in the microejection device, tubing, and pump, Additional and/or refining features arise from the dependent claims.

BRIEF DESCRIPTION OF THE DRAWINGS

The present invention will now be described in more detail with reference to schematic drawings, which merely represent exemplary embodiments and are not to restrict the extent of the present invention.

DETAILED DESCRIPTION OF THE INVENTION

Figure 1:
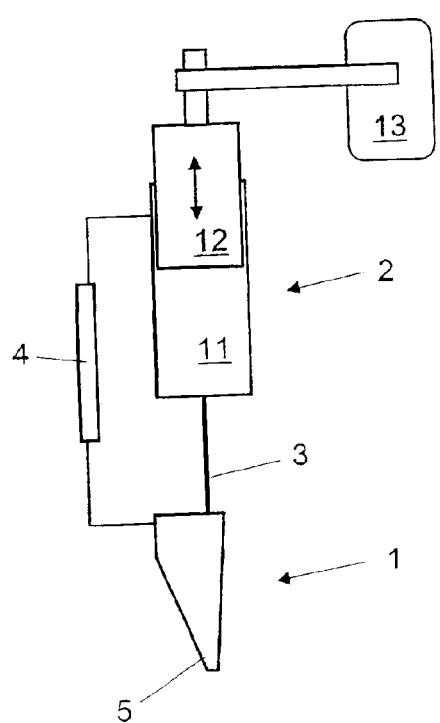
FIG. 1 shows a system for aspirating and/or dispensing liquid samples according to a first embodiment.

FIGS. 1 to 4 show a system for aspirating and/or dispensing liquid samples. This system, which is designed as a pipettor, comprises a microejection device 1 and a pump 2, which are connected with one another via tubing 3. In addition, the system comprises a computer 4 for loading an activatable computer program product. When this computer program product has been loaded into computer 4 and activated, it allows this computer 4 to control and synchronize the following functions of the system:

Active definition of a sample volume and dispensing of this defined sample volume with the microejection device 1, which is filled with sample liquid;

Tracking of a part 12, 12', 12", which conveys the liquid, of the pump 2 around a value, dependent on this sample volume, which is defined and is actively dispensed only by the microejection device 1, to prevent excessive pressure differences in the microejection device 1, tubing 3, and pump 2.

FIG. 1 shows a system for aspirating and/or dispensing liquid samples, according to a first embodiment, in which microejection device 1 comprises an endpiece 5 implemented as a microejection pump. In this embodiment, a microejection device 1 implemented as a piezoelectric micropump is preferred.

Figure 2:
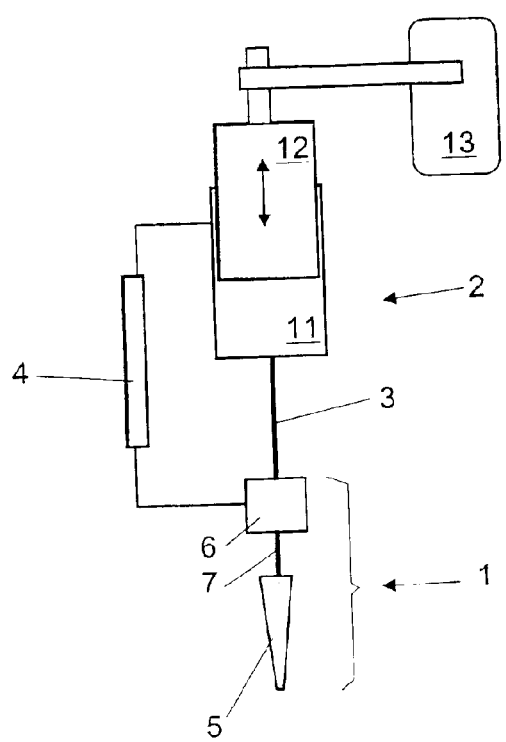
FIG. 2 shows a system for aspirating and/or dispensing liquid samples according to a second embodiment.

FIG. 2 shows a system for aspirating and/or dispensing liquid samples according to a second embodiment, in which microejection device 1 comprises an endpiece 5, implemented as a disposable pipette tip, a pulse generator 6, and tubing 7 which connects an endpiece 5 and pulse generator 6. The pulse generator, whose functional principle is known from, for example, U.S. Pat. No. 5,763,278, triggers pressure waves in tubing 7, which cause the liquid droplets to be driven out of endpiece 5—implemented in U.S. Pat. No. 5,763,278 as a needle.

Figure 3:
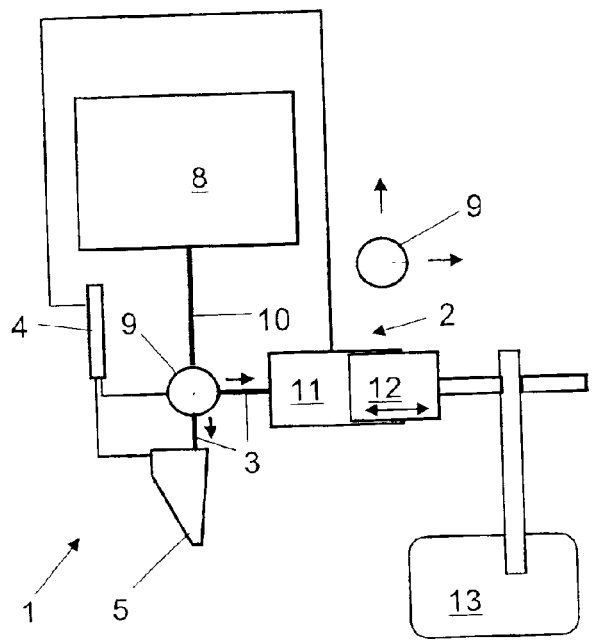
FIG. 3 shows a system for aspirating and/or dispensing liquid samples according to third embodiment.

FIG. 3 shows a system for aspirating and/or dispensing liquid samples according to a third embodiment, in which microejection device 1 comprises an endpiece 5 implemented as a microejection pump. In this embodiment, a microejection device 1 in the form of a piezoelectric micropump is preferred. This embodiment additionally comprises a reservoir 8 and/or a three-way valve 9, with three-way valve 9 being positioned between pump 2 and reservoir 8. Reservoir 8 and three-way valve 9 and pump 2 are connected with one another via tubing 10. Notwithstanding the illustration in FIG. 3, the liquid transport can occur from microejection device 1 into pump 2 and from pump 2 in the direction of reservoir 8 via two separate valves (not illustrated in the Figure).

The first three embodiments share the feature that pump 2 is a piston pump that comprises a cylinder 11, a piston 12, and a drive 13. Among the many possible pumps for highly precise aspirating and dispensing of liquids, a commercially available device with the name "CAVRO XP3000 plus Modular Digital Pump", which is sold by the firm Cavro Scientific Instruments Inc., Sunnyvale, Calif., USA, has, for example, proven itself.

Figure 4:
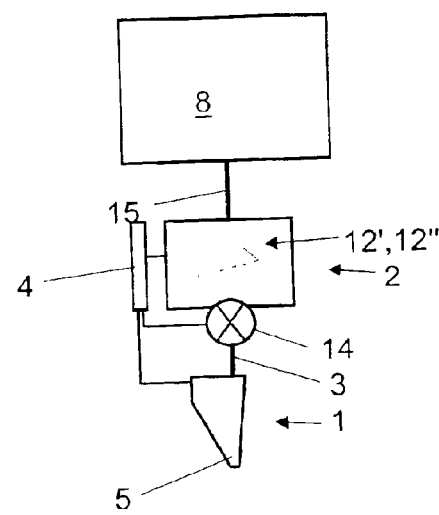
FIG. 4 shows a system for observing and/or dispensing liquid samples according to a fourth embodiment.

FIG. 4 shows a system for aspirating and/or dispensing of liquid samples according to a fourth embodiment, in which microejection device 1 comprises an endpiece 5 implemented as a microejection pump. In this embodiment, a microejection device 1 in the form of a micropump and endpiece is preferred. Preferred micropumps function, for example, according to the piezoelectric principle or according to the principle of thermal actuation. This embodiment additionally comprises a reservoir 8 and/or a valve 14, with valve 14 being positioned between pump 2 and microejection device 1. Reservoir 8 and pump 2 are connected with one another via tubing 15. Pump 2 is not a piston pump in this case, in which a piston 12 represents the part of the pump that conveys the liquid, but another conveyance device for liquids that operates according to the pass-through principle. Such pumps are, for example, squeeze pumps or peristaltic pumps, which deform (squeeze) a tube 12" filled with a liquid using rollers 12' and thus perform transportation of the liquid. Such peristaltic pumps are known from many other laboratory devices for supplying liquids (e.g. in heart/lung machines etc.). Such pumps typically operate less precisely than the preferred piston pump "CAVRO XP3000 plus Modular Digital Pump".

All of these exemplary embodiments preferably include the use of a non-compressible system liquid for relaying the liquid movements in a way known to those with skill in the art.

One embodiment of the methods provided according to the present invention—on which this system, as well as the computer program product, are based—permits pumps to be used that can operate less precisely and are therefore more economical, such as a squeeze and/or peristaltic pump. This method for synchronization of the system for aspirating and/or dispensing liquid samples that comprises a microejection device 1 and a pump 2, which are connected with one another via tubing 3, with the system being assigned a computer 4 for loading an activatable computer program product for synchronizing microejection device 1 and pump 2, is characterized in that computer 4 controls and synchronizes the following functions of the system on the basis of the activated computer program product:

Active definition of a sample volume and dispensing of this defined sample volume with microejection device 1, which is filled with sample liquid;

Tracking of a part 12, 12', 12", which conveys the liquid, of pump 2 around a value, dependent on this sample volume, which is defined and is actively dispensed only by the microejection device 1, to prevent excessive pressure differences in microejection device 1, tubing 3, and pump 2.

The dispensing of the sample volume preferably occurs in volume-defined partial steps. The special geometric dimensions and physical properties of the microejection pumps used allow reproducible dispensing of liquid samples with a volume of a few nanoliters. The active displacement of liquid from microejection device 1 causes a slight drop in pressure in tubing 3 and/or 7. Although part of this drop in pressure can possibly be compensated by the use of flexible tubing 3, 7, this drop in pressure is nonetheless not to exceed a maximum value. The amount of this maximum value depends on the individual characteristics of an appropriately constructed pipettor. In a prototype of the applicant, this maximum value was defined at 100 nL of error volume.

The method according to the present invention at least approximately compensates for this error volume by tracking part 12, 12', 12" of pump 2 that conveys the liquid. This tracking can occur continuously or in partial steps. Tracking in partial steps is preferred, with the partial steps for the tracking of part 12, 12', 12" of pump 2 that conveys the liquid being combined into step series. A step series in this case always includes the same number of conveyance steps, preferably eight partial steps. If a "CAVRO XP3000 plus Modular Digital Pump" is used, then 3.000 steps and/or 24.000 partial steps can be completed by means of a highly precise stepping motor used as drive 13. Eight of these partial steps are preferably combined into one step, so that only one whole-number multiple of 8 partial steps has to be executed. The dispensing time of a specific sample volume results from the individual droplet volume and the dispensing frequency of microejection device 1. The computer according to the present invention thus controls the tracking of part 12, 12', 12" of pump 2 which conveys the liquid in such a way that it occurs uniformly over the entire dispensing time. The displacement volume (one stroke) of such a pump is preferably 50 to 500 µl. From this, at a displacement volume of, for example, 50 µl in cylinder 11 of a pump 2, volumes of 2.1 nl per partial step and/or 16.7 nl per step result. At a displacement volume of 500 µl, the volumes are greater by a factor of 10.

The beginning of the tracking of the part of the pump which conveys the liquid can occur with a time shift relative to the beginning of the dispensing of the sample volume: if the tracking begins somewhat before the beginning of dispensing, excess pressure is built up in tubing 3 and/or 7, which is advantageous for the separation of higher viscosity liquids, such as dimethyl sulfoxide (DMSO). If the tracking begins somewhat after the beginning of dispensing, a negative pressure is built up in tubing 3 and/or 7, which is advantageous for the separation of very low viscosity liquids, such as acetone.

The end of the tracking of the part of the pump which conveys the liquid can occur with a time delay relative to the end of the dispensing of the sample volume: if the tracking ends somewhat before the end of dispensing, a drop in pressure results in tubing 3 and/or 7 as dispensing finishes, which successfully prevents dripping of very low viscosity liquids. If the tracking ends somewhat after dispensing is finished, excess pressure is built up in tubing 3 and/or 7, which is advantageous for subsequent separation of higher viscosity liquids, such as DMSO.

Merely by temporally varying the driving of microejection device 1 and pump 2, the system can be individually adjusted to the liquid to be pipetted and/or dispensed. If a residual volume arises in liquids with a viscosity less than or equal to water through the dispensing of the sample volume and the tracking of the part of the pump which conveys the liquid in partial steps, it has been proven for dispensing and tracking to thus be adjusted to one another in such a way that this residual volume is always borne by the tracking of the part of the pump which conveys liquid, i.e. that a smaller drop in pressure is always generated between pump 2 and microejection device 1. This residual volume was determined in practice for a pipettor and should be smaller than 100 nL. In order that residual volumes cannot add up in larger series of dispensed samples and possibly impair the functioning and/or the reproducibility of a pipettor or dispenser, a value corresponding to the residual volume is preferably stored in computer 4 and taken into consideration in a following dispensation of samples.

The present invention also comprises a corresponding system, such as a pipettor and/or dispenser for performing this method. A machine of this type can have one or more individually drivable channels, each with an endpiece 5. Endpieces 5 and/or the pipette tips can be positioned either in a two-dimensional or in a three-dimensional array.

All embodiments share the feature that the computer 4 is integrated into the system as an electronic component. However, the computer could also be part of an external computer that is made available to the system. An integrated computer has the advantage, however, that it can be implemented very compactly—e.g. as a single board equipped with microelectronic elements in the housing of a pipettor or even in a pump integrated therein. The computer is preferably able to be externally operated and read out, regardless of whether it is integrated in the system or is made available to the system, in order that, for example, automatic protocols about the liquid samples aspirated and/or dispensed can be drawn up.

The computer program product according to the present invention for synchronization of a system of this type for aspirating and/or dispensing liquid samples as described above can be loaded in a computer 4, which can be made available to the system or which is already integrated in the system, and activated there. In addition, it can be stored on in any typical data carrier for electronic systems for data processing, such as a hard drive, a "floppy disk", a "compact disc" (CD), a "digital versatile disc" (DVD), but also in a "read-only memory" (ROM), a "random access memory" (RAM), or similar things, and can be retrieved from there. The computer program product according to the present invention is able to communicate with other programs and/or computers. It can also include commands for controlling a three-way valve 9, which is connected upstream from pump 2, and/or commands for controlling pump 2 for the aspiration of a liquid.

The computer program product according to the present invention thus serves for making a computer 4 capable of synchronizing a system for aspirating and/or dispensing liquid samples, with the system comprising a microejection device 1 and a pump 2, which are connected with one another via tubing 3—regardless of whether computer 4 is only made available to the system for this purpose or is integrated therein. At the same time, this computer program can already be loaded in the computer and/or installed in a memory of the computer. In its activated state, the computer program product makes computer 4 capable of controlling and synchronizing the following functions of the system:

Active definition of a sample volume and dispensing of this defined sample volume with the microejection device 1, which is filled with sample liquid;

Tracking of a part 12, 12', 12", which conveys the liquid, of pump 2 around a value, dependent on this sample volume, which is defined and is actively dispensed only by microejection device 1, to prevent excessive pressure differences in microejection device 1, tubing 3, and pump 2.

The functioning of devices (and/or systems) according to the present invention and methods according to the present invention can be performed with three independent methods, as follows.

A. Optical Measurements

By means of a high-speed camera, the individual droplets that were dispensed with a microejection device 1 could be measured directly. With a device as shown in FIG. 1, liquid was aspirated and dispensed in the multipipetting mode. 43 aliquots of 25 nl each (=1075 nl total volume dispensed) were dispensed, with each aliquot consisting of 48 individual droplets. Each individual droplet was measured individually.

| Intended volume | Average volume of the 43 aliquots | ACC of the aliquots | CV of the aliquots |
|---|---|---|---|
| 25 nl | 26.5 nl | 5.9% | 1.91% |

| Average volume of all individual droplets (n = 2064) | CV over all individual droplets (n = 2064) |
|---|---|
| 551.6 pl | 2.9% |

B Gravimetric Measurements

Liquid was aspirated and dispensed in the multipipetting mode (12 aliquots) with a device as shown in FIG. 1. The volumes were determined with a Mettler UMT2 scale (measurement range 0.1 $\mu$g to 2.1 g). 90% dimethyl sulfoxide was pipetted. 100, 500, and 1000 individual droplets, respectively, (intended droplet volume=400 pl) were dispensed. A density of 1.09 g/ml was assumed for the evaluation.

| | Multipipetting Mode | | |
|---|---|---|---|
| Intended volume | Average volume of the 12 aliquots | ACC of the aliquots | CV of the aliquots |
| 40 nl | 40.7 nl | 1.8% | 1.9% |
| 80 nl | 82.0 nl | 2.5% | 2.3% |
| 400 nl | 409.4 nl | 2.3% | 1.1% |

C. Photometric Measurements

Liquid was pipetted both in the single pipetting mode (12 single pipettings each) and in the multipipetting mode (12 aliquots) with a device as shown in FIG. 1. 20, 100, 200, or 1000 individual droplets, (intended droplet volume=500 pl) respectively, were dispensed.

An aqueous 0.25 M $FeSO_4$ solution with FerroZine® was used for the calibration curve. "FerroZine®" is the registered trademark of Hach Company, P.O. Box 389, Loveland, Colo. 80539 USA. The resulting complex solution was stabilized with ascorbic acid. From this initial solution, measurement solutions were produced by dilution, corresponding to pipetting volumes of 2.5 nl, 5.0 nl, 10.0 nl, 20.0 nl, 40.0 nl, and 80.0 nl in 200 pi. 12 aliquots of 200 $\mu$l each of these measurement solutions were pipetted by hand into a microplate and the optical absorption and/or the optical densities (OD) were measured with a microplate photometry reader. The calibration curve was calculated through the measurement points by means of linear regression.

For the volume determinations, 100 $\mu$l at a time of a 3.25 mM FerroZine® solution with ascorbic acid buffered with ammonium acetate was placed into the wells of a microplate. 10 nl and 50 nl of a 0.25 M $FeSO_4$ solution stabilized with ascorbic acid was pipetted into this with the pipettor. The pipettings of 100 nl and 500 nl were performed with a 0.025 M $FeSO_4$ solution stabilized with ascorbic acid.

After the pipetting procedure, the volume was topped up with demineralized water in the individual wells to 200 $\mu$l total volume. The optical absorption of the colored complex solution in the wells of a microplate was then measured in a microplate photometry reader and the volumes were calculated with reference to the calibration curve.

| Intended volume | Average volume of the 12 aliquots | ACC of the aliquots | CV of the aliquots |
|---|---|---|---|
| | Single Pipetting Mode | | |
| 10 nl | 9.7 nl | 3.0% | 2.9% |
| 50 nl | 48.0 nl | 4.0% | 1.2% |
| 100 nl | 101.8 nl | 1.8% | 1.5% |
| 500 nl | 497.5 nl | 0.5% | 1.5% |
| | Multipipetting Mode | | |
| 10 nl | 9.8 nl | 2.0% | 1.4% |
| 50 nl | 48.1 nl | 3.8% | 2.5% |
| 100 nl | 99.3 nl | 0.7% | 4.0% |
| 500 nl | 509.0 nl | 1.8% | 2.8% |

The object initially stated, to suggest alternative devices and methods that allow both economical and highly reproducible separation of volumes in the nanoliter to picoliter range, is thus fulfilled.

What is claimed is:

1. A system for aspirating and/or dispensing of liquid samples that comprises a microejection device and a pump, which are connected with one another via tubing, wherein the pump is accomplished as a piston pump comprising a pump cylinder, a pump piston, and a pump drive, and wherein this system comprises a computer that is capable of being loaded with an activatable computer program product for synchronizing operation of the microejection device and the pump, wherein the system carries out the following functions because of the computer program product loaded and activated into the computer to control and synchronize the system:

a) to actively define sample volumes until a maximum under-pressure is reached in the tubing, using only the microejection device, which is filled with sample liquid;

b) dispense the sample volumes defined in (a) using only the microejection device, which is filled with sample liquid; and c) to track the piston of the pump that conveys liquid about a tracking value that is dependent on the sample volume, which is defined in (a) and is actively dispensed only by the microejection device in (b); wherein said tracking value is maximized at an error volume.

2. The system according to claim 1, wherein the maximum under-pressure in the tubing as defined in (a) corresponds to an error volume of 100 nL, and wherein a residual volume is smaller than 100 nL.

3. The system according to claim 1 or 2, wherein the computer is integrated into the system as an electronic component that can also be externally operated and read out can be obtained therefrom.

4. The system according to claim 1 or 2, wherein the microejection device comprises an endpiece that is a microejection pump.

5. The system according to claim 1 or 2, wherein the microejection device is a piezoelectric micropump.

6. The system according to claim 1 or 2, wherein the microejection device further comprises an endpiece that is a disposable pipette tip, a pulse generator, and tubing connecting the endpiece and pulse generator.

7. The system according to claim 1 or 2, further comprising a reservoir, a three-way valve, or a reservoir and a three-way valve, with the three-way valve located between the pump and the reservoir, and the reservoir, the three-way valve and the pump being connected with one another by tubing.

8. A method for synchronizing a system for aspirating and/or dispensing liquid samples, wherein the system comprises a microejection device and a pump connected with one another by tubing, wherein the pump is accomplished as a piston pump comprising a pump cylinder, a pump piston, and a pump drive, and wherein the system further comprises a computer that includes a loaded activatable computer program product that synchronizes the microejection device and the pump, wherein the loaded and activated computer program product directs the computer to control and synchronize the system, the method comprising:

a) actively defining sample volumes until a maximum under-pressure is reached in the tubing, using only the microejection device, which is filled with sample liquid;

b) dispensing the sample volumes defined in (a) using only the microejection device, which is filled with sample liquid; and c) tracking the piston of the pump that conveys liquid about a tracking value that is dependent on the sample volume, which is defined in (a) and is actively dispensed only by the microejection device in (b); wherein said tracking value is maximized at an error volume.

9. The method according to claim 8, wherein the maximum under-pressure in the tubing as defined in (a) corresponds to an error volume of 100 nL, and wherein a residual volume is smaller than 100 nL.

10. The method according to claim 8 or 9, wherein dispensing of the sample volume occurs in volume-defined partial steps.

11. The method according to claim 8 or 9, wherein tracking of the piston of the pump occurs continuously or in partial steps.

12. The method according to claim 8 or 9, wherein tracking of the piston of the pump occurs in partial steps, said partial steps are collected into series of steps, with a series of steps always comprising the same number of partial steps.

13. The method according to claim 8 or 9, wherein the beginning or the end of the tracking of the piston of the pump occurs with a time shift relative to the beginning or the end of dispensing of the sample volume.

14. The method according to claim 8 or 9, wherein, where a residual volume occurs due to the dispensing of the sample volume and the tracking of the piston of the pump in partial steps, dispensing and tracking are adjusted to one another so that this residual volume is always borne by the tracking of the piston of the pump.

15. The method according to claim 8 or 9, wherein a value corresponding to a residual volume is stored in the computer and is taken into account in dispensing samples following occurrence of the residual volume.

16. A computer program product for synchronizing a system for aspirating and/or dispensing liquid samples, wherein the system comprises a microejection device and a pump that are connected with one another by tubing, wherein the pump is accomplished as a piston pump comprising a pump cylinder, a pump piston and a pump drive, and wherein the system further comprises a computer wherein the computer is capable of being loaded with activatable computer program product for synchronizing operation of the microejection device and the pump, and wherein this computer program product, in its activated state, enables the computer to control and synchronize the system:

a) to actively define sample volumes until a maximum under-pressure is reached in the tubing, using only the microejection device, which is filled with sample liquid;

b) dispense the sample volumes defined in (a) using only the microejection device, which is filled with sample liquid; and c) to track the piston of the pump that conveys the liquid about a tracking value that is dependent on the sample volume, which is defined in (a) and is actively dispensed only by the microejection device in (b) wherein said tracking value is maximized at an error volume.

17. The computer program product according to claim 16, further comprising commands for controlling a three-way valve, connected upstream from the pump.

18. The computer program product according to claim 16 or 17, further comprising commands for controlling the pump for the aspiration of a liquid.

19. The method of claim 12, wherein the number of partial steps is 8 steps.

* * * * *